United States Patent
Diianni et al.

(10) Patent No.: US 11,684,713 B2
(45) Date of Patent: *Jun. 27, 2023

(54) FLUID DELIVERY DEVICE, TRANSCUTANEOUS ACCESS TOOL AND INSERTION MECHANISM FOR USE THEREWITH

(71) Applicant: Insulet Corporation, Acton, MA (US)

(72) Inventors: Steven Diianni, Danvers, MA (US); Ian McLaughlin, Groton, MA (US); Jason O'Connor, Acton, MA (US); Robert Campbell, Waltham, MA (US); Kevin Schmid, Boxford, MA (US)

(73) Assignee: INSULET CORPORATION, Acton, MA (US)

( * ) Notice: Subject to any disclaimer, the term of this patent is extended or adjusted under 35 U.S.C. 154(b) by 572 days.

This patent is subject to a terminal disclaimer.

(21) Appl. No.: 16/796,853

(22) Filed: Feb. 20, 2020

(65) Prior Publication Data
US 2020/0188581 A1    Jun. 18, 2020

Related U.S. Application Data

(63) Continuation of application No. 16/194,873, filed on Nov. 19, 2018, now Pat. No. 10,569,011, which is a
(Continued)

(51) Int. Cl.
*A61M 5/145* (2006.01)
*A61B 5/145* (2006.01)
(Continued)

(52) U.S. Cl.
CPC ..... *A61M 5/14566* (2013.01); *A61B 5/14532* (2013.01); *A61B 5/14865* (2013.01);
(Continued)

(58) Field of Classification Search
CPC .... A61M 2005/247; A61M 2005/2407; A61M 5/19; A61M 5/2466; A61M 5/288;
(Continued)

(56) References Cited

U.S. PATENT DOCUMENTS

| 303,013 A | 8/1884 | Horton |
|---|---|---|
| 306,691 A | 10/1884 | Johnson |

(Continued)

FOREIGN PATENT DOCUMENTS

| DE | 420595 C | 10/1925 |
|---|---|---|
| DE | 19723648 C1 | 8/1998 |

(Continued)

OTHER PUBLICATIONS

US 5,954,699 A, 09/1999, Jost et al. (withdrawn)
(Continued)

*Primary Examiner* — Tiffany Legette-Thompson
(74) *Attorney, Agent, or Firm* — Goodwin Procter LLP

(57) ABSTRACT

Disclosed is a fluid delivery device including a fluid reservoir and a transcutaneous access tool fluidly coupled to the fluid reservoir, wherein the transcutaneous access tool includes a needle or a trocar. The fluid delivery device may further include a transcutaneous access tool insertion mechanism for deploying the transcutaneous access tool, wherein the insertion mechanism is configured to insert and retract the needle/trocar in a single, uninterrupted motion.

18 Claims, 5 Drawing Sheets

Related U.S. Application Data continuation of application No. 13/854,445, filed on Apr. 1, 2013, now Pat. No. 10,130,758, which is a continuation of application No. PCT/US2013/034674, filed on Mar. 29, 2013.

(60) Provisional application No. 61/618,028, filed on Mar. 30, 2012.

(51) Int. Cl.

| | |
|---|---|
| *A61B 5/1486* | (2006.01) |
| *A61M 5/142* | (2006.01) |
| *F04B 9/02* | (2006.01) |
| *A61M 5/172* | (2006.01) |
| *A61M 5/158* | (2006.01) |
| *A61M 5/32* | (2006.01) |
| *A61M 5/14* | (2006.01) |

(52) U.S. Cl.
CPC ...... *A61M 5/1452* (2013.01); *A61M 5/14244* (2013.01); *A61M 5/14248* (2013.01); *A61M 5/158* (2013.01); *A61M 5/1723* (2013.01); *F04B 9/02* (2013.01); *A61M 5/3291* (2013.01); *A61M 2005/1403* (2013.01); *A61M 2005/14252* (2013.01); *A61M 2005/14506* (2013.01); *A61M 2230/201* (2013.01); *F04C 2270/041* (2013.01)

(58) Field of Classification Search
CPC ............... A61M 5/158; A61M 5/1452; A61M 5/14248; A61M 5/14244; A61M 5/14566; A61M 2005/14252; A61M 2005/14506; A61B 5/14532; A61B 5/14865
See application file for complete search history.

(56) References Cited

U.S. PATENT DOCUMENTS

| | | |
|---|---|---|
| 315,727 A | 4/1885 | Church |
| 405,524 A | 6/1889 | Benton |
| 410,817 A | 9/1889 | Weeks, Jr. |
| 2,667,986 A | 2/1954 | Perelson |
| 3,631,847 A | 1/1972 | Hobbs |
| 3,792,703 A | 2/1974 | Moorehead |
| 3,812,843 A | 5/1974 | Wootten et al. |
| 3,841,328 A | 10/1974 | Jensen |
| 3,885,662 A | 5/1975 | Schaefer |
| 4,067,000 A | 1/1978 | Carlson |
| 4,151,845 A | 5/1979 | Clemens |
| 4,152,098 A | 5/1979 | Moody et al. |
| 4,193,397 A | 3/1980 | Tucker et al. |
| 4,211,998 A | 7/1980 | Junginger et al. |
| 4,231,019 A | 10/1980 | Junginger et al. |
| 4,261,388 A | 4/1981 | Shelton |
| 4,268,150 A | 5/1981 | Chen |
| 4,276,170 A | 6/1981 | Vaillancourt |
| 4,342,311 A | 8/1982 | Whitney et al. |
| 4,346,385 A | 8/1982 | Schiavone et al. |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| 4,855,746 A | 8/1989 | Stacy |
| 4,858,619 A | 8/1989 | Toth |
| 4,871,351 A | 10/1989 | Feingold |
| 4,882,600 A | 11/1989 | Van de Moere |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,944,659 A | 7/1990 | Labbe et al. |
| 4,969,874 A | 11/1990 | Michel et al. |
| 4,973,998 A | 11/1990 | Gates |
| 4,985,016 A | 1/1991 | Theeuwes et al. |
| 4,994,047 A | 2/1991 | Walker et al. |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,125,415 A | 6/1992 | Bell |
| 5,176,662 A | 1/1993 | Bartholomew et al. |
| 5,178,609 A | 1/1993 | Ishikawa |
| 5,189,609 A | 2/1993 | Tivig et al. |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,244,463 A | 9/1993 | Cordner, Jr. et al. |
| 5,245,447 A | 9/1993 | Stemmle |
| 5,254,096 A | 10/1993 | Rondelet et al. |
| 5,257,980 A | 11/1993 | Van Antwerp et al. |
| 5,261,884 A | 11/1993 | Stern et al. |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,411,480 A | 5/1995 | Kriesel |
| 5,433,710 A | 7/1995 | VanAntwerp et al. |
| 5,452,033 A | 9/1995 | Balling et al. |
| 5,492,534 A | 2/1996 | Athayde et al. |
| 5,503,628 A | 4/1996 | Fetters et al. |
| 5,505,709 A | 4/1996 | Funderburk et al. |
| 5,507,288 A | 4/1996 | Bocker et al. |
| 5,514,096 A | 5/1996 | Hiejima |
| 5,533,389 A | 7/1996 | Kamen et al. |
| 5,545,152 A | 8/1996 | Funderburk et al. |
| 5,573,342 A | 11/1996 | Patalano |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,613,956 A | 3/1997 | Patterson et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,665,065 A | 9/1997 | Colman et al. |
| 5,665,070 A | 9/1997 | McPhee |
| 5,685,859 A | 11/1997 | Kornerup |
| 5,693,018 A | 12/1997 | Kriesel et al. |
| 5,695,490 A | 12/1997 | Flaherty et al. |
| 5,702,363 A | 12/1997 | Flaherty |
| 5,704,520 A | 1/1998 | Gross |
| 5,716,343 A | 2/1998 | Kriesel et al. |

(56) References Cited

U.S. PATENT DOCUMENTS

| | | |
|---|---|---|
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,764,159 A | 6/1998 | Neftel |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,800,420 A | 9/1998 | Gross et al. |
| 5,810,015 A | 9/1998 | Flaherty |
| 5,814,020 A | 9/1998 | Gross |
| 5,840,063 A | 11/1998 | Flaherty |
| 5,845,218 A | 12/1998 | Altschul |
| 5,848,990 A | 12/1998 | Cirelli et al. |
| 5,848,991 A | 12/1998 | Gross et al. |
| 5,851,197 A | 12/1998 | Marano et al. |
| 5,858,005 A | 1/1999 | Kriesel |
| 5,858,239 A | 1/1999 | Kenley et al. |
| 5,865,806 A | 2/1999 | Howell |
| 5,871,470 A | 2/1999 | McWha |
| 5,875,393 A | 2/1999 | Altschul et al. |
| 5,878,539 A | 3/1999 | Grubb |
| 5,885,659 A | 3/1999 | Takahashi et al. |
| 5,885,808 A | 3/1999 | Spooner et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,921,419 A | 7/1999 | Niedospial, Jr. et al. |
| 5,931,814 A | 8/1999 | Alex et al. |
| 5,935,099 A | 8/1999 | Peterson et al. |
| 5,954,058 A | 9/1999 | Flaherty |
| 5,954,694 A | 9/1999 | Sunseri |
| 5,957,859 A | 9/1999 | Rosenfeld |
| 5,957,890 A | 9/1999 | Mann et al. |
| 5,961,492 A | 10/1999 | Kriesel et al. |
| 5,965,848 A | 10/1999 | Altschul et al. |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,024,539 A | 2/2000 | Blomquist |
| 6,050,978 A | 4/2000 | Orr et al. |
| 6,071,292 A | 6/2000 | Makower et al. |
| 6,090,092 A | 7/2000 | Fowles et al. |
| 6,126,637 A | 10/2000 | Kriesel et al. |
| 6,144,847 A | 11/2000 | Altschul et al. |
| 6,152,898 A | 11/2000 | Olsen |
| 6,174,300 B1 | 1/2001 | Kriesel et al. |
| 6,190,359 B1 | 2/2001 | Heruth |
| 6,200,338 B1 | 3/2001 | Solomon et al. |
| 6,206,850 B1 | 3/2001 | ONeil |
| 6,244,776 B1 | 6/2001 | Wiley |
| 6,244,778 B1 | 6/2001 | Chesbrough |
| 6,309,370 B1 | 10/2001 | Haim et al. |
| 6,363,609 B1 | 4/2002 | Pickren |
| 6,375,639 B1 | 4/2002 | Duplessie et al. |
| 6,475,196 B1 | 11/2002 | Vachon |
| 6,520,936 B1 | 2/2003 | Mann |
| 6,527,744 B1 | 3/2003 | Kriesel et al. |
| 6,569,125 B2 | 5/2003 | Jepson et al. |
| 6,572,542 B1 | 6/2003 | Houben et al. |
| 6,572,585 B2 | 6/2003 | Choi |
| 6,666,852 B2 | 12/2003 | Niedospial, Jr. |
| 6,699,221 B2 | 3/2004 | Vaillancourt |
| 6,740,059 B2 | 5/2004 | Flaherty |
| 6,883,778 B1 | 4/2005 | Newton et al. |
| 7,008,404 B2 | 3/2006 | Nakajima |
| 7,018,360 B2 | 3/2006 | Flaherty et al. |
| 7,025,744 B2 | 4/2006 | Utterberg et al. |
| 7,060,059 B2 | 6/2006 | Keith et al. |
| 7,128,727 B2 | 10/2006 | Flaherty et al. |
| 7,144,384 B2 | 12/2006 | Gorman et al. |
| 7,160,272 B1 | 1/2007 | Eyal et al. |
| 7,267,665 B2 | 9/2007 | Steil et al. |
| 7,291,133 B1 | 11/2007 | Kindler et al. |
| 7,303,549 B2 | 12/2007 | Flaherty et al. |
| 7,918,825 B2 | 4/2011 | OConnor et al. |
| 9,402,950 B2 | 8/2016 | Dilanni et al. |
| 2001/0053895 A1 | 12/2001 | Vaillancourt |
| 2002/0010423 A1 | 1/2002 | Gross et al. |
| 2002/0032374 A1 | 3/2002 | Holker et al. |
| 2002/0066715 A1 | 6/2002 | Niedospial |
| 2002/0123740 A1 | 9/2002 | Flaherty et al. |
| 2003/0163097 A1 | 8/2003 | Fleury et al. |
| 2004/0010207 A1 | 1/2004 | Flaherty et al. |
| 2004/0064088 A1 | 4/2004 | Gorman et al. |
| 2004/0088224 A1 | 5/2004 | Mukai |
| 2004/0092865 A1 | 5/2004 | Flaherty et al. |
| 2004/0116847 A1 | 6/2004 | Wall |
| 2004/0158208 A1 | 8/2004 | Hiejima |
| 2004/0203357 A1 | 10/2004 | Nassimi |
| 2005/0020980 A1 | 1/2005 | Inoue et al. |
| 2005/0187524 A1 | 8/2005 | Willis et al. |
| 2005/0203461 A1* | 9/2005 | Flaherty ............ A61M 5/14248 604/890.1 |
| 2005/0238507 A1 | 10/2005 | Dilanni et al. |
| 2005/0258581 A1 | 11/2005 | Tanaka |
| 2006/0134323 A1 | 6/2006 | OBrien |
| 2006/0155210 A1 | 7/2006 | Beckman et al. |
| 2006/0178633 A1 | 8/2006 | Garibotto et al. |
| 2006/0204535 A1 | 9/2006 | Johnson |
| 2006/0253085 A1 | 11/2006 | Geismar et al. |
| 2006/0282290 A1 | 12/2006 | Flaherty et al. |
| 2007/0005018 A1 | 1/2007 | Tekbuchava |
| 2007/0025811 A1 | 2/2007 | Wilhelm |
| 2007/0112332 A1 | 5/2007 | Harding et al. |
| 2007/0118405 A1 | 5/2007 | Campbell et al. |
| 2007/0129690 A1 | 6/2007 | Rosenblatt et al. |
| 2007/0173974 A1 | 7/2007 | Lin |
| 2007/0197163 A1 | 8/2007 | Robertson |
| 2007/0282269 A1 | 12/2007 | Carter et al. |
| 2008/0004515 A1 | 1/2008 | Jennewine |
| 2008/0006500 A1 | 1/2008 | Spahr |
| 2008/0051738 A1 | 2/2008 | Griffin |
| 2008/0065050 A1 | 3/2008 | Sparks et al. |
| 2008/0078400 A1 | 4/2008 | Martens et al. |
| 2008/0132880 A1 | 6/2008 | Buchman |
| 2008/0183060 A1* | 7/2008 | Steil ...... A61B 5/4839 606/151 |
| 2008/0249508 A1 | 10/2008 | Lopez et al. |
| 2008/0287906 A1 | 11/2008 | Burkholz et al. |
| 2009/0054866 A1 | 2/2009 | Teisen-Simony et al. |
| 2009/0062767 A1 | 3/2009 | Van Antwerp et al. |
| 2009/0069787 A1 | 3/2009 | Estes et al. |
| 2009/0099521 A1 | 4/2009 | Gravesen et al. |
| 2009/0124979 A1 | 5/2009 | Raymond et al. |
| 2009/0198215 A1 | 8/2009 | Chong et al. |
| 2009/0299300 A1 | 12/2009 | Truitt et al. |
| 2010/0137784 A1 | 6/2010 | Cefai et al. |
| 2010/0152658 A1 | 6/2010 | Hanson et al. |
| 2010/0241086 A1* | 9/2010 | Yodfat ................ A61B 5/4839 604/246 |
| 2011/0054390 A1 | 3/2011 | Searle et al. |
| 2011/0054399 A1 | 3/2011 | Chong et al. |
| 2011/0144586 A1 | 6/2011 | Michaud et al. |
| 2011/0166512 A1 | 7/2011 | Both et al. |
| 2011/0230833 A1 | 9/2011 | Landman et al. |
| 2011/0251509 A1 | 10/2011 | Beyhan et al. |
| 2011/0316562 A1 | 12/2011 | Cefai et al. |
| 2012/0003093 A1 | 1/2012 | Lischer et al. |
| 2012/0003935 A1 | 1/2012 | Lydon et al. |
| 2012/0010594 A1 | 1/2012 | Holt et al. |
| 2012/0078161 A1 | 3/2012 | Masterson et al. |
| 2012/0109066 A1 | 5/2012 | Chase et al. |
| 2012/0238851 A1 | 9/2012 | Kamen et al. |

(56) References Cited

U.S. PATENT DOCUMENTS

| | | |
|---|---|---|
| 2012/0277668 A1 | 11/2012 | Chawla |
| 2013/0060233 A1 | 3/2013 | OConnor et al. |
| 2013/0178791 A1 | 7/2013 | Javitt |
| 2013/0317753 A1 | 11/2013 | Kamen et al. |
| 2014/0074033 A1 | 3/2014 | Sonderegger et al. |
| 2014/0127048 A1 | 5/2014 | Dilanni et al. |
| 2014/0128839 A1 | 5/2014 | Dilanni et al. |
| 2014/0135880 A1 | 5/2014 | Baumgartner et al. |
| 2014/0316379 A1 | 10/2014 | Sonderegger et al. |
| 2016/0015891 A1 | 1/2016 | Papiorek |
| 2016/0038689 A1 | 2/2016 | Lee et al. |
| 2016/0302054 A1 | 10/2016 | Kimura et al. |
| 2017/0128664 A1 | 5/2017 | Diianni et al. |

FOREIGN PATENT DOCUMENTS

| | | |
|---|---|---|
| DE | 19920896 A1 | 11/2000 |
| EP | 0341049 A2 | 11/1989 |
| EP | 342947 A2 | 11/1989 |
| EP | 0496305 A2 | 7/1992 |
| EP | 0763369 A1 | 3/1997 |
| EP | 0867196 A2 | 9/1998 |
| EP | 0937475 A2 | 8/1999 |
| EP | 2397181 A1 | 12/2011 |
| EP | 2830499 A1 | 2/2015 |
| GB | 875034 A | 8/1961 |
| GB | 2443261 A | 4/2008 |
| TW | 200740148 A | 10/2007 |
| TW | M452390 U | 5/2013 |
| WO | 8101658 A1 | 6/1981 |
| WO | 8606796 A1 | 11/1986 |
| WO | 9800193 A1 | 1/1998 |
| WO | 9801071 A1 | 1/1998 |
| WO | 9856293 A1 | 12/1998 |
| WO | 9910040 A1 | 3/1999 |
| WO | 9956803 A1 | 11/1999 |
| WO | 9962576 A1 | 12/1999 |
| WO | 0019887 A1 | 4/2000 |
| WO | 0029047 A1 | 5/2000 |
| WO | 0029049 A1 | 5/2000 |
| WO | 0030705 A1 | 6/2000 |
| WO | 0061215 A1 | 10/2000 |
| WO | 0074752 A1 | 12/2000 |
| WO | 0078210 A1 | 12/2000 |
| WO | 0152727 A1 | 7/2001 |
| WO | 0156633 A2 | 8/2001 |
| WO | 015663 | 9/2001 |
| WO | 0176684 A1 | 10/2001 |
| WO | 0220073 A2 | 3/2002 |
| WO | 0226282 | 4/2002 |
| WO | 0240083 A2 | 5/2002 |
| WO | 2002068823 | 9/2002 |
| WO | 2003030984 A1 | 4/2003 |
| WO | 03090509 A2 | 11/2003 |
| WO | 200172354 A2 | 11/2003 |
| WO | 2002015954 A1 | 11/2003 |
| WO | 2006053007 A2 | 5/2006 |
| WO | 2007064835 A2 | 6/2007 |
| WO | 2008024810 A2 | 2/2008 |
| WO | 2008133702 A1 | 11/2008 |
| WO | 2009098648 A2 | 8/2009 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012134589 A1 | 10/2012 |
| WO | 2013078200 A1 | 5/2013 |
| WO | 2013134486 A2 | 9/2013 |
| WO | 2013149186 A1 | 10/2013 |
| WO | 2013182321 A1 | 12/2013 |
| WO | 2014099404 A1 | 6/2014 |
| WO | 2014194183 A2 | 12/2014 |
| WO | 2015061493 A1 | 4/2015 |
| WO | 2015081337 A2 | 6/2015 |
| WO | 2016141082 A1 | 9/2016 |
| WO | 2017205816 A1 | 11/2017 |

OTHER PUBLICATIONS

International Search Report and Written Opinion for PCT Application No. PCT/US2022/015985, dated May 30, 2022, 13 pages.
International Search Report and Written Opinion of PCT/US2018/018901, dated Aug. 6, 2018, 12 pages.
International Search Report and Written Opinion for application No. PCT/US2017/015601, dated May 16, 2017, 12 pages.
International Search Report and Written Opinion for application No. PCT/US18/52464, dated Jan. 4, 2019, 11 pages.
International Preliminary Report on Patentability dated Oct. 9, 2014, issued in PCT Patent Application No. PCT/US2013/034674, 15 pages.
U.S. Office Action dated Mar. 31, 2015, issued in U.S. Appl. No. 13/854,456, 11 pages.
U.S. Office Action dated Aug. 4, 2015, issued in U.S. Appl. No. 13/854,463 11 pages.
U.S. Office Action dated Sep. 23, 2015, issued in U.S. Appl. No. 13/854,456, 13 pages.
Notice of Allowance dated Mar. 25, 2016, issued in U.S. Appl. No. 13/854,456, 9 pages.
Notice of Allowance dated May 21, 2018, issued in U.S. Appl. No. 13/854,463, 7 pages.
U.S. Office Action dated May 31, 2016, issued in U.S. Appl. No. 13/854,463, 16 pages.
U.S. Office Action dated Oct. 31, 2017, issued in U.S. Appl. No. 13/854,463 13 pages.
U.S. Office Action dated Mar. 3, 2017, issued in U.S. Appl. No. 13/854,463, 12 pages.
EPO Search Report dated Nov. 11, 2015, received in corresponding Application No. 13768938.6, 7 pgs.
European Patent Office, "Notification of Transmittal of the ISR and the Written Opinion of the International Searching Authority, or the Declaration," in PCT Application No. IPCT/GB2015/050248, dated Jun. 23, 2015, 12 pages.
Web-Site Brochure dated Jan. 4, 2000. "The Glucose Sensor".www.animascorp.com/sensor_f.html.
Web-Site Brochure dated Dec. 20, 1999. Applied Medical Technology.• "508 Pump Information", www.applied-medical.co.uk/508.htm.
Notice of Allowance dated May 23, 2018, issued in U.S. Appl. No. 13/854,445, 8 pages.
U.S. Office Action dated May 17, 2016, issued in U.S. Appl. No. 13/854,445, 11 pages.
U.S. Office Action dated Oct. 31, 2017, issued in U.S. Appl. No. 13/854,445, 15 pages.
U.S. Office Action dated Jan. 25, 2017, issued in U.S. Appl. No. 13/854,445, 23 pages.
International Search Report for the International Patent Application No. PCT/US03/16640, dated Oct. 2, 2003, 1 page.
User's Guide for Model 508 Insulin Pump, Mini Med, Aug. 2000, 145 pages.
Web-Site Brochure dated Jan. 4, 2000. SOOIL-Homepage. "Portable Insulin Pump", www.sooil.com/product2.htm.
Web-Site Brochure dated Jan. 4, 2000. SOOIL-Homepage. "Portable Insulin Pump".www.sooil.com/product3.htm.
Web-Site Brochure dated Jan. 4, 2000. SOOIL-Homepage. "Portable Insulin Pump", www.sooil.com/product4.htm.
Web-Site Brochure dated Dec. 20, 1999. "The Animas R-1000 Insulin Pump", www.animascorp.com/pump_f_s.html.
Web-Site Brochure dated Dec. 20, 1999. "The Animas R-1000 Insulin Pump" www.animascorp.com/pump_f_f.html.
Web-Site Brochure dated Jan. 4, 2000. SOOIL-Homepage. "Portable Insulin Pump".www.sooil.com/intro2.htm.
Web-Site Brochure dated Jan. 4, 2000. MiniMed 508. "Doing its job. Naturally." www.minimed.com/files/mm113.htm.

(56) References Cited

OTHER PUBLICATIONS

International Preliminary Report on Patentability dated Apr. 9, 2020, issued in PCT Patent Application No. PCT/US2018/052464, 7 pages.

* cited by examiner

FLUID DELIVERY DEVICE, TRANSCUTANEOUS ACCESS TOOL AND INSERTION MECHANISM FOR USE THEREWITH

CROSS-REFERENCE TO RELATED APPLICATIONS

This application is a continuation of U.S. patent application Ser. No. 16/194,873, filed Nov. 19, 2018, which is a continuation of U.S. patent application Ser. No. 13/854,445, filed Apr. 1, 2013, which is a continuation of PCT Application No. PCT/US13/34674, filed Mar. 29, 2013, which claims the benefit of U.S. Provisional Application No. 61/618,028, filed Mar. 30, 2012. The contents of the aforementioned applications are incorporated herein by reference in their entirety.

TECHNICAL FIELD

The present invention relates to fluid delivery devices for delivering therapeutic liquids to a patient, and more particularly, to an infusion pump for delivering therapeutic liquids to a patient.

BACKGROUND INFORMATION

Fluid delivery devices have numerous uses such as delivering a liquid medicine or other therapeutic fluid to a patient subcutaneously. In a patient with diabetes mellitus, for example, ambulatory infusion pumps have been used to deliver insulin to a patient. These ambulatory infusion pumps have the ability to offer sophisticated fluid delivery profiles including variable basal rates and bolus requirements. The ability to carefully control drug delivery can result in better efficacy of the drug and therapy and less toxicity to the patient.

Some existing ambulatory infusion pumps include a reservoir to contain the liquid medicine and use electromechanical pumping or metering technology to deliver the liquid medicine via tubing to a needle and/or soft cannula that is inserted subcutaneously into the patient. These existing devices allow control and programming via electromechanical buttons or switches located on the housing of the device. The devices include visual feedback via text or graphic screens and may include alert or warning lights and audio or vibration signals and alarms. Such devices are typically worn in a harness or pocket or strapped to the body of the patient.

Some infusion pumps have been designed to be relatively small, low cost, light-weight, and easy-to-use. One example of such a pump is the OMNIPOD® insulin infusion pump available from Insulet Corporation. Examples of infusion pumps are also described in greater detail, for example, in U.S. Pat. Nos. 7,128,727; 7,018,360; and 7,144,384 and U.S. Patent Application Publication Nos. 2007/0118405, 2006/0282290, 2005/0238507, and 2004/0010207, which are fully incorporated herein by reference. These pumps include insertion mechanisms for causing a transcutaneous access tool, such as a needle and/or soft cannula, to be inserted into a patient. Although such pumps are effective and provide significant advantages over other insulin infusion pumps, the design of the insertion mechanism may be improved, for example, to reduce the size of the pump, to improve the comfort to the user, and/or to incorporate continuous glucose monitoring (CGM). These pumps also include fluid driving mechanisms for driving fluid from a reservoir through the transcutaneous access tool. The fluid driving mechanisms may also be improved to facilitate assembly and use of the pump.

SUMMARY

The present disclosure provides various fluid delivery devices to deliver a liquid medicine or other therapeutic fluid to a patient subcutaneously. In certain embodiments the fluid delivery device may comprise an ambulatory insulin infusion device to administer insulin to a patient. The fluid delivery device may include one or more batteries for providing a power source, a fluid reservoir for holding a fluid, a fluid drive mechanism for driving the fluid out of the reservoir, a fluid passage mechanism for receiving the fluid from the reservoir and passing the fluid to a destination via a transcutaneous access tool, and a transcutaneous access tool insertion mechanism for deploying the transcutaneous access tool.

In certain embodiments, the transcutaneous access tool includes a needle/trocar, and the transcutaneous access tool insertion mechanism is configured to insert and retract the needle/trocar in a single, uninterrupted motion. In such a manner, the pain of insertion and retraction of the needle/trocar experienced by the patient may be reduced.

In certain embodiments, the fluid delivery device may comprise a fluid reservoir; a transcutaneous access tool fluidly coupled to the fluid reservoir, the transcutaneous access tool including a needle/trocar; and a transcutaneous access tool insertion mechanism for deploying the transcutaneous access tool, wherein the insertion mechanism is configured to insert and retract the needle/trocar in a single, uninterrupted motion.

In certain embodiments, the fluid delivery device may comprise a fluid reservoir; a transcutaneous access tool fluidly coupled to the fluid reservoir, the transcutaneous access tool including at least a needle/trocar; and a transcutaneous access tool insertion mechanism for deploying the transcutaneous access tool, wherein the insertion mechanism is configured to insert the needle/trocar with an increasing insertion force as the needle/trocar moves in an insertion direction.

In certain embodiments, the transcutaneous access tool insertion mechanism for deploying a transcutaneous access tool including a cannula and a needle/trocar located inside of the cannula may comprise a first sliding member configured to move the needle/trocar in an insertion direction and a retraction direction; a second sliding member configured to move the cannula in the insertion direction; a torsion spring; and linkages coupled between the torsion spring and the first sliding member such that energy stored in the torsion spring causes the linkages to move the first sliding member in the insertion direction and the retraction direction.

BRIEF DESCRIPTION OF THE DRAWINGS

These and other features and advantages will be better understood by reading the following detailed description, taken together with the drawings wherein.

DETAILED DESCRIPTION

Figures 1, 2:
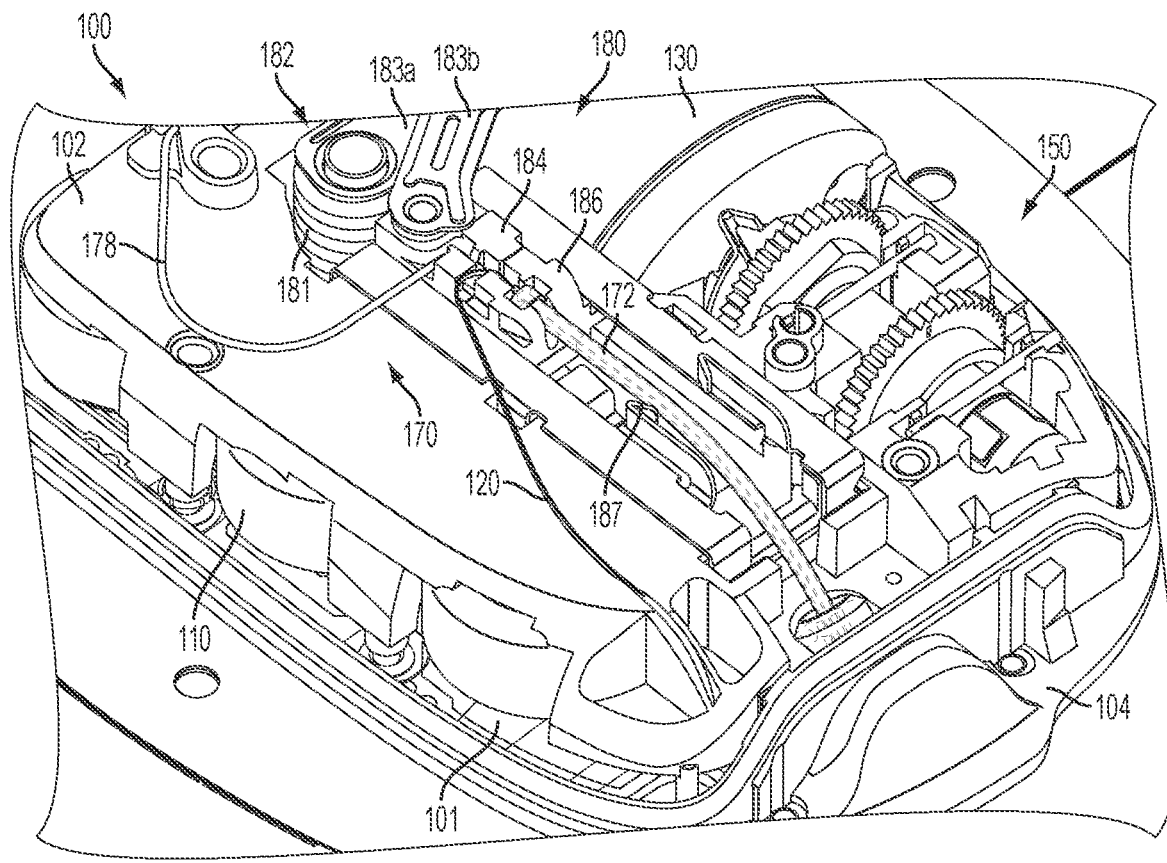
FIG. 1 is a top perspective view of a fluid delivery device with a transcutaneous access tool insertion mechanism in a pre-deployment position, consistent with the present disclosure.
FIG. 2 is a bottom perspective view of a needle and cannula retracted into the fluid delivery device in the pre-deployment position shown in FIG. 1.
Figure 3:
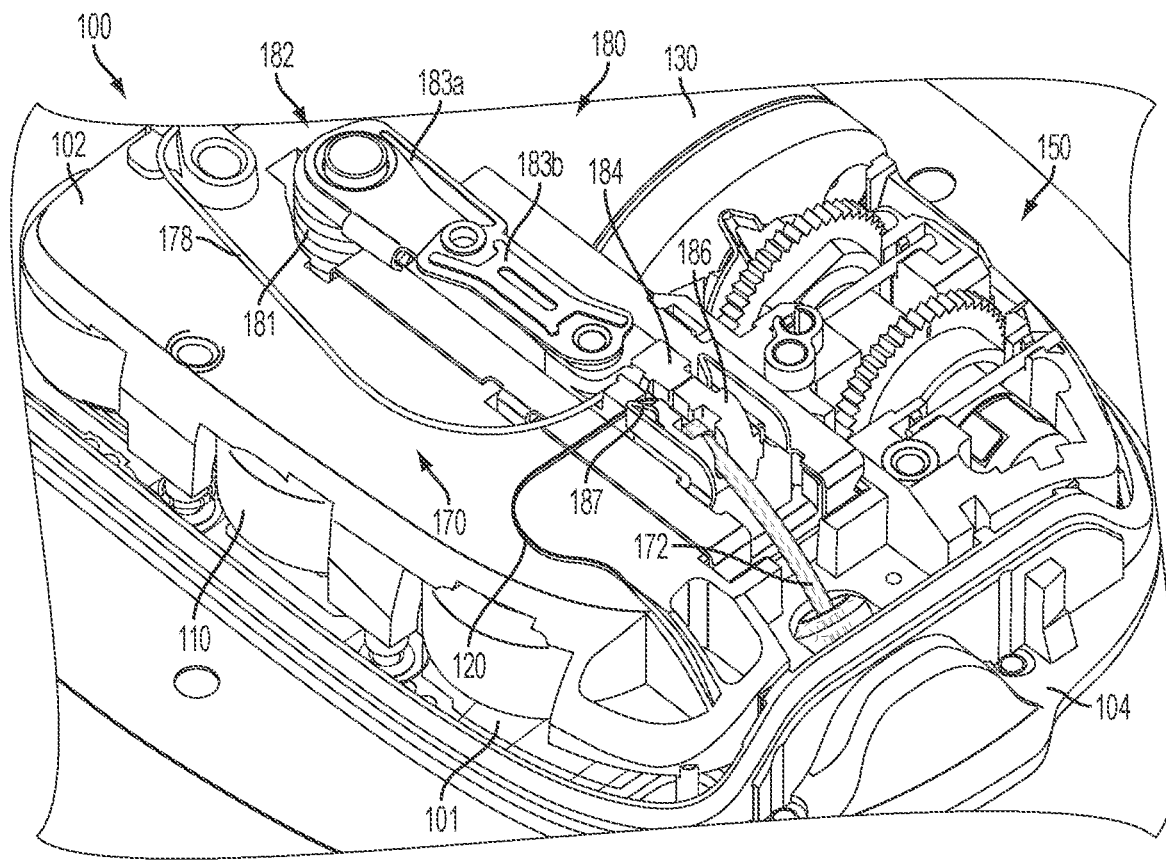
FIG. 3 is a top perspective view of the fluid delivery device shown in FIG. 1 with the insertion mechanism in an intermediate position.
Figure 4:
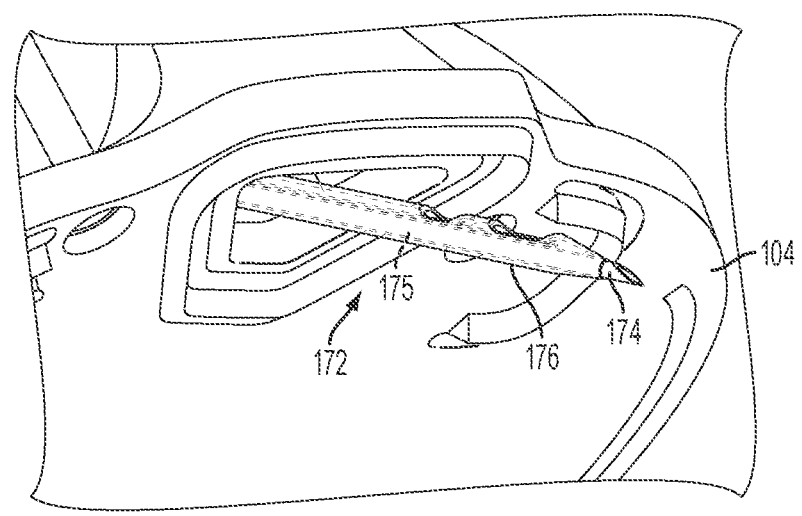
FIG. 4 is a bottom perspective view of the needle and cannula extending from the fluid delivery device in the intermediate position shown in FIG. 3.

A fluid delivery device, consistent with embodiments of the present disclosure, may be used to deliver a therapeutic fluid (e.g. a liquid medicine) to a patient via a transcutaneous access tool, such as a needle/trocar and/or a cannula. A transcutaneous access tool insertion mechanism may be used to deploy the transcutaneous access tool, for example, by inserting and retracting a needle/trocar in a single, uninterrupted motion. The insertion mechanism may also provide an increasing insertion force as the needle/trocar moves in the insertion direction. The fluid delivery device may also include a clutch mechanism to facilitate filling a reservoir and engagement of a drive mechanism for driving fluid out of the reservoir. In certain embodiments, the fluid delivery device may comprise an ambulatory insulin infusion device.

In other embodiments, a fluid delivery device may be used to deliver a therapeutic fluid to a patient with integrated monitoring, such as continuous glucose monitoring (CGM). In these embodiments, the fluid deliver device may include a transcutaneous access tool configured to introduce a monitoring test strip through the skin of the patient, for example, using one or more needles, cannulas and/or trocars.

Referring to FIGS. 1-6, one embodiment of a fluid delivery device 100 is shown and described. In the exemplary embodiment, the fluid delivery device 100 is used to subcutaneously deliver a fluid, such as a liquid medicine (e.g. insulin), to a person or an animal. Those skilled in the art will recognize that the fluid delivery device 100 may be used to deliver other types of fluids. The fluid delivery device 100 may be used to deliver fluids in a controlled manner, for example, according to fluid delivery profiles accomplishing bolus requirements, continuous infusion and variable flow rate delivery.

According to one embodiment, the fluid delivery device 100 may include one or more batteries 110 for providing a power source, a fluid reservoir 130 for holding a fluid, a fluid drive mechanism 150 for driving the fluid out of the reservoir 130, a fluid passage mechanism 170 for receiving the fluid from the reservoir 130 and passing the fluid to a destination via a transcutaneous access tool 172, and a transcutaneous access tool insertion mechanism 180 for deploying the transcutaneous access tool 172. The fluid delivery device 100 may include a circuit board 101 with control circuitry for controlling the device and a chassis 102 that provides mechanical and/or electrical connections between components of the fluid deliver device 100. The fluid delivery device 100 may also include a housing 104 to enclose the circuit board 101, the chassis 102, and the components 110, 130, 150, 170, 180.

The fluid delivery device 100 may also include integrated monitoring such as continuous glucose monitoring (CGM). A monitor test strip 120 coupled to a monitor (not shown) in the device 100 may be introduced by the transcutaneous access tool 172 subcutaneously. One example of the monitor test strip is a CGM test strip (such as the type available from Nova Biomedical) which may be understood as a glucose sensor configured to test for a concentration level of glucose in the blood of a patient. The fluid delivery device 100 may be configured to receive data from the monitoring test strip concerning a glucose level of the patient, and determining an output of insulin from the reservoir based on the glucose level.

The transcutaneous access tool 172 includes an introducer trocar or needle 174 at least partially positioned within a lumen 175 of a cannula 176 (e.g., a soft flexible cannula), which is capable of passing the fluid into the patient. In particular, the introducer needle/trocar 174 may initially penetrate the skin such that both the introducer needle/trocar 174 and the cannula 176 are introduced (inserted) into the patient, and the introducer needle/trocar 174 may then be retracted within the cannula 176 such that the cannula 176 remains inserted. A fluid path, such as tubing 178, fluidly couples the reservoir 130 to the lumen 175 of cannula 176 of the transcutaneous access tool 172.

Figure 5:
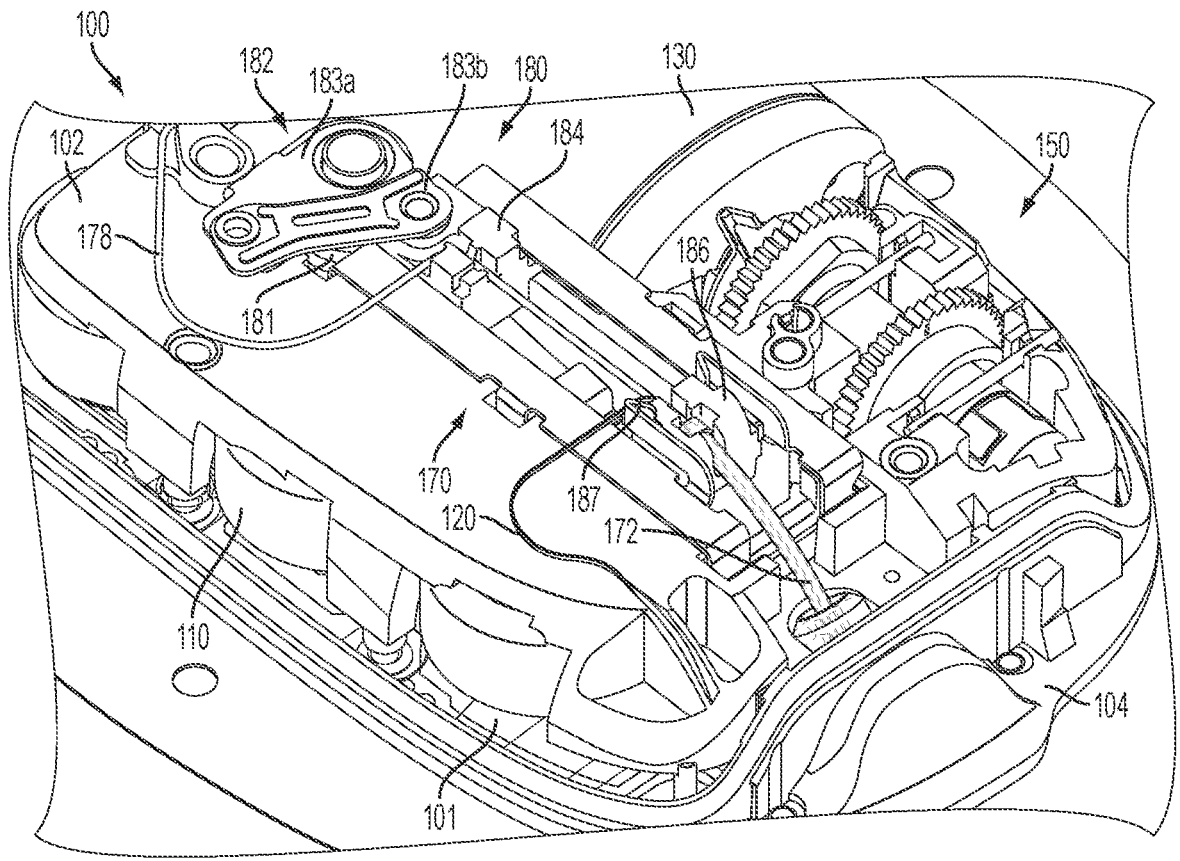
FIG. 5 is a top perspective view of the fluid delivery device shown in FIG. 1 with the insertion mechanism in a post-deployment position.
Figure 6:
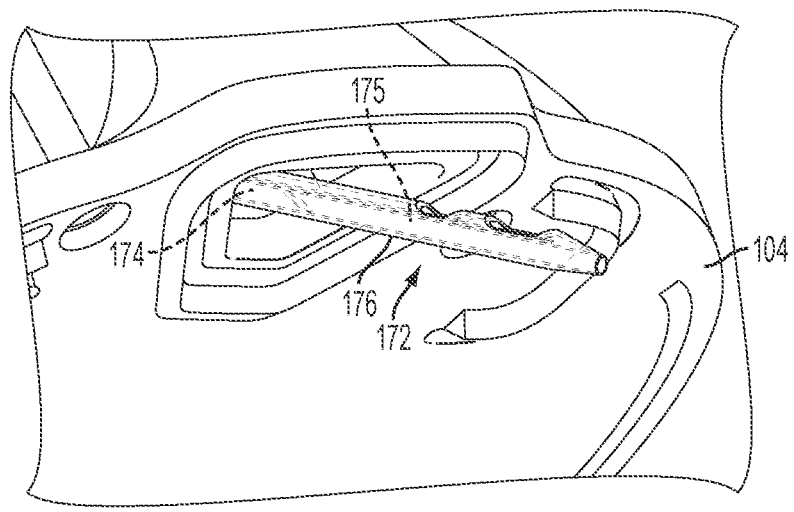
FIG. 6 is a bottom perspective view of the cannula extending from the fluid delivery device in the post-deployment position shown in FIG. 5.

The transcutaneous access tool insertion mechanism 180 is coupled to the transcutaneous access tool 172 to deploy the transcutaneous access tool 172, for example, by inserting the needle/trocar 174 and cannula 176 through the skin of a patient and retracting the needle/trocar 174. In the illustrated embodiment, the insertion mechanism 180 includes a spring-biased linkage mechanism 182 and sliding members 184, 186 coupled to the needle/trocar 174 and cannula 176, respectively, for moving the needle/trocar 174 and cannula 176 in the insertion direction and for moving the needle/trocar 174 in the retraction direction. In a single, uninterrupted motion, the spring-biased linkage mechanism 182 moves from a pre-deployment position (FIG. 1) with both needle/trocar 174 and cannula 176 retracted (FIG. 2) to an intermediate position (FIG. 3) with both needle/trocar 174 and cannula 176 inserted (FIG. 4) to a post-deployment position (FIG. 5) with the needle/trocar 174 retracted and the cannula 176 inserted (FIG. 6).

One embodiment of the spring-biased linkage mechanism 182 includes a helical torsion spring 181 and first and second linkages 183a, 183b coupled between the torsion spring 181 and the first sliding member 184. Energy stored in the torsion spring 181 applies a force to the linkages 183a, 183b, which applies a force to the first sliding member 184 to move the first sliding member 184 in both the insertion direction and in the retraction direction. In the pre-deployment position (FIG. 1), the torsion spring 181 is loaded and the sliding members 184, 186 are locked and prevented from moving. When the sliding members 184, 186 are released, the energy stored in the torsion spring 181 causes the first linkage 183a to rotate (e.g., clockwise as shown), which applies a force to the first sliding member 184 through the second linkage 183b causing the first sliding member 184 with the needle/trocar 174 to move (with the second sliding member 186) in the insertion direction. In the intermediate position (FIG. 3), the linkages 183a, 183b are fully extended with the needle/trocar 174 and cannula 176 being inserted, the second sliding member 186 is locked, and the remaining energy stored in the torsion spring 181 causes the first linkage 183a to continue to rotate, which applies an opposite force to the first sliding member 184 through the second linkage 183b causing the first sliding member 184 with the needle/trocar 174 to move in the retraction direction to the post-deployment position (FIG. 5). In the illustrated embodiment, the second sliding member 186 is locked against retraction by one or more latches 187. Thus, in the foregoing manner, the continuous uninterrupted clockwise rotation of first linkage 183a via the energy of torsion spring 181 provides the transcutaneous access tool insertion mechanism 180 with the ability to insert and retract the needle/trocar 174 in a single, uninterrupted motion.

The spring-biased linkage mechanism 182 allows a single spring and motion to achieve both the insertion and retraction and has a relatively small size. The spring-biased linkage mechanism 182 also reduces the static stresses caused by locking and holding back the sliding members 184, 186 and provides a smoother and more comfortable needle/trocar insertion because of the way the linkages 183a, 183b vector the forces applied to the sliding members 184, 186. The static forces on the sliding members 184, 186 are relatively small in the pre-deployment position when the linkages 183a, 183b are fully retracted. When the deployment starts and the linkages 183a, 183b start to become extended, the insertion forces increase because the force vectors increase in the insertion direction as the linkages extend 183a, 183b until a maximum insertion force is reached at the fully extended, intermediate position. By gradually increasing the insertion forces, the needle/trocar insertion and retraction is smoother, quieter and less painful.

Figure 7:
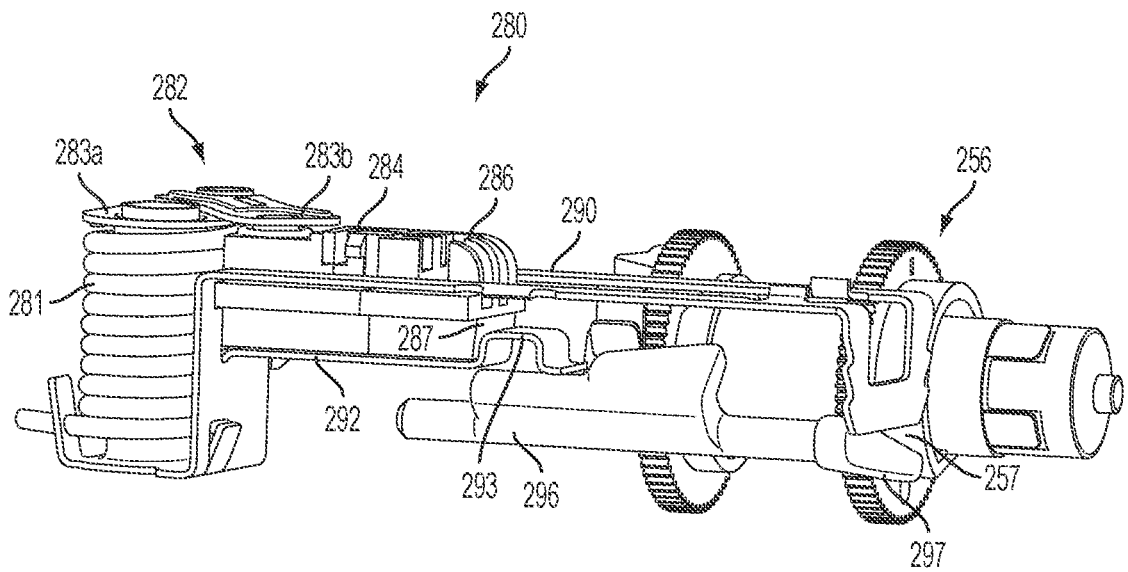
FIG. 7 is a side perspective view of another embodiment of the insertion mechanism, consistent with the present disclosure, in a pre-deployment position.
Figure 8:
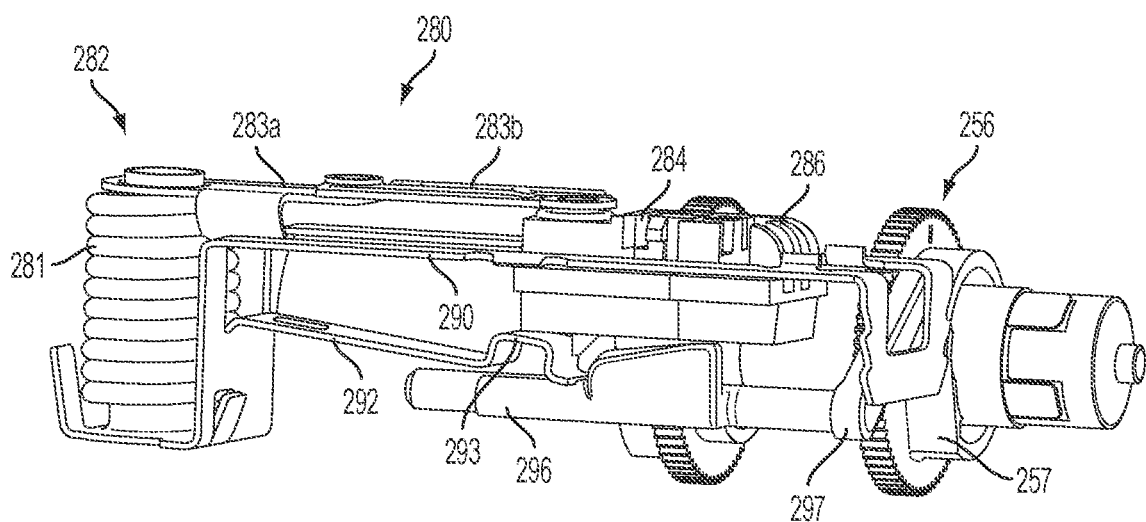
FIG. 8 is a side perspective view of the insertion mechanism shown in FIG. 7 in an intermediate position.

Another embodiment of an insertion mechanism 280 is shown in greater detail in FIGS. 7-10. The sliding members 284, 286 are slidably received in a frame 290 and moved by a spring-biased linkage mechanism 282 including torsion spring 281 and linkages 283a, 283b. In this embodiment, a cam finger 292 (e.g., extending from the frame 290) engages beneath one or both of the sliding members 284, 286 to lock the sliding members in the retracted or pre-deployment position (FIG. 7). In this pre-deployment position, the cam finger 292 is held against the sliding members 284, 286 by a release bar 296, which may be moved (rotated) to allow the cam finger 292 to move and release the sliding members 284, 286 (FIG. 8). The cam finger 292 may be biased in a downward direction and/or the second sliding member 286 may include a cam surface 287 to help facilitate movement along the cam finger 292 over locking mechanism 293 upon actuation.

The release bar 296 includes a lever 297 for pivoting the release bar 296 between an engaged position against the cam finger 292 (FIG. 7) and a disengaged position releasing the cam finger 292 (FIG. 8). The release bar 296 may be biased toward the disengaged position and held against the cam finger 292 in the engaged position until the lever 297 is released allowing the release bar 296 to move to the disengaged position. In the illustrated embodiment, the lever 297 engages a rotating surface 257 of a drive wheel 256 of the fluid drive mechanism 150 such that the lever 297 is held in the engaged position for part of the rotation and is released at a certain point during the rotation (e.g., when a flat portion of the rotating surface 257 allows the lever 297 to move).

Figure 9:
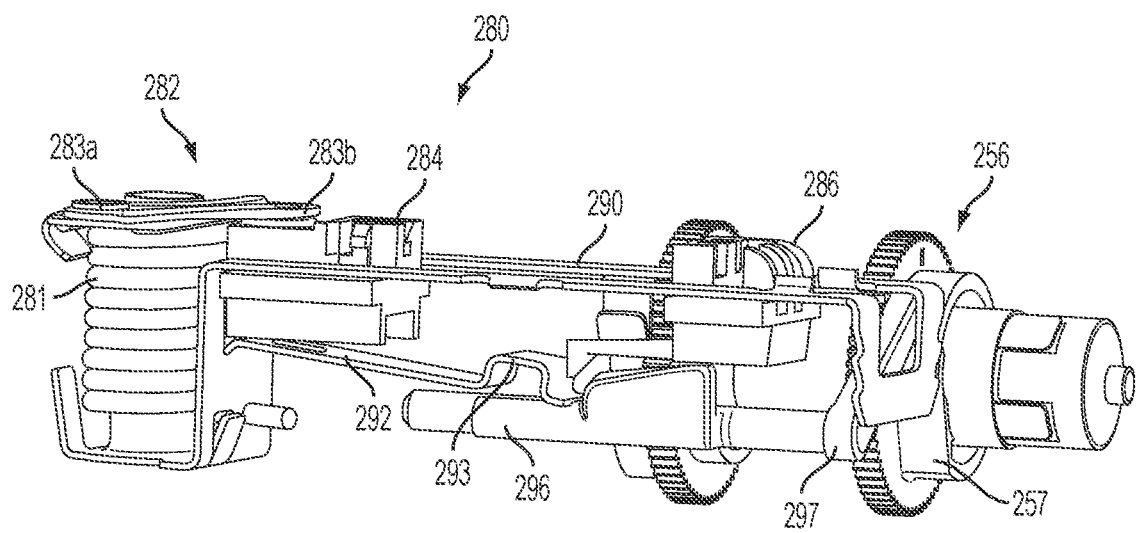
FIG. 9 is a side perspective view of the insertion mechanism shown in FIG. 7 in a post-deployment position.
Figure 10:
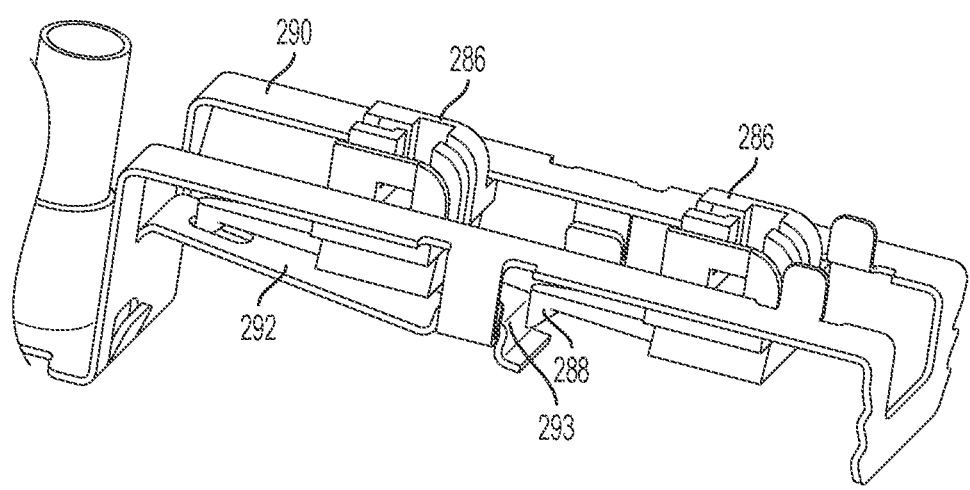
FIG. 10 is a top perspective view of the second sliding member of the insertion mechanism shown in FIG. 7 locked in the pre-deployment and post-deployment positions.

As shown in FIGS. 9 and 10, the cam finger 292 may also be used to lock the second sliding member 286 in the insertion position. A locking portion 288 of the second sliding member 286 engages a locking portion 293 of the cam finger 292 when the linkage mechanism 282 is fully extended in the intermediate position and prevents the second sliding member 286 from retracting such that the cannula remains inserted. As discussed above, the second sliding member 286 may also be locked by one or more latches 187 (shown in FIGS. 1-6) extending from a top of the frame 290.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A fluid delivery device, comprising: a fluid reservoir; a transcutaneous access tool fluidly coupled to the fluid reservoir, the transcutaneous access tool including a needle and a cannula; a glucose monitoring device, wherein the fluid reservoir, the transcutaneous access tool, and the glucose monitoring device are located within a housing, and wherein at least a portion of the transcutaneous access tool and the glucose monitoring device are configured to extend from the housing and into a patient; and an insertion and retraction mechanism within the housing, the insertion and retraction mechanism comprising: a spring defining a longitudinal axis; and a first linkage and a second linkage coupled between the spring and a first sliding member, wherein the first sliding member is coupled with the needle, wherein the first and second linkages are configured to move the first sliding member in an insertion direction and a retraction direction in response to a force from the spring, and wherein the first linkage includes a first end adjacent the spring and a second end directly coupled to the second linkage; and a frame operable to lock the first sliding member and a second sliding member in a pre-deployment position and to lock the second sliding member in a post-deployment position, wherein the needle is located within the cannula such that the cannula remains deployed when the needle is retracted.

2. The fluid delivery device of claim 1, wherein the insertion and retraction mechanism is configured to increase an insertion force as the needle moves in the insertion direction.

3. The fluid delivery device of claim 1, wherein the glucose monitoring device comprises a test strip extending through the cannula.

4. The fluid delivery device of claim 3, wherein the test strip is positioned between the first and second sliding members.

5. The fluid delivery device of claim 1, wherein the frame is configured to slidably receive the first sliding member and the second sliding member.

6. The fluid delivery device of claim 5, wherein the frame includes a cam finger operable to lock the first and second sliding members in the pre-deployment position and to lock the second sliding member in the post-deployment position.

7. The fluid delivery device of claim 6, wherein the insertion and retraction mechanism further comprises a release bar configured to hold the cam finger when the cam finger locks the first and second sliding members in the pre-deployment position and configured to release the cam finger to allow the first and second sliding members to move in the insertion direction.

8. A fluid delivery device, comprising:
a fluid reservoir;
a transcutaneous access tool fluidly coupled to the fluid reservoir, the transcutaneous access tool including a cannula, and a trocar located inside the cannula;
a glucose monitoring device extending through the cannula;
an insertion mechanism configured to deploy at least a portion of the transcutaneous access tool and the glucose monitoring device into a patient, the insertion mechanism comprising:
a first sliding member coupled with the trocar;
a second sliding member adjacent the first sliding member, the second sliding member coupled with the cannula and operable to move the cannula in an insertion direction; and
linkages coupled between a torsion spring and the first sliding member, wherein the torsion spring and the linkages are operable to move the first sliding member in the insertion direction and a retraction direction.

9. The fluid delivery device of claim 8, wherein the insertion mechanism is operable to insert the trocar with an increasing insertion force from the torsion spring as the trocar moves in the insertion direction.

10. The fluid delivery device of claim 8, wherein the trocar is located within the cannula, and wherein the cannula is operable to remain deployed when the trocar is retracted.

11. The fluid delivery device of claim 8, wherein the insertion mechanism further comprises a frame slidably receiving the first and second sliding members and operable to lock the first and second sliding members in a pre-deployment position and to lock the second sliding member in a post-deployment position.

12. The fluid delivery device of claim 8, wherein the glucose monitoring device comprises a flexible test strip.

13. The fluid delivery device of claim 12, wherein the flexible test strip extends between the trocar and a chassis.

14. A transcutaneous access tool insertion and retraction mechanism, comprising:
a needle located within a cannula;
a first sliding member coupled with the needle and operable to move the needle in an insertion direction and in a retraction direction;
a second sliding member coupled with the cannula and operable to move the cannula in the insertion direction, wherein a glucose monitoring device extends between the first and second sliding members; and
a first linkage and a second linkage coupled between a torsion spring and the first sliding member such that, upon deployment, energy stored in the torsion spring causes the first and second linkages to cooperate to move the first sliding member in the insertion direction and the retraction direction.

15. The transcutaneous access tool insertion and retraction mechanism of claim 14, further comprising a frame slidably receiving the first and second sliding members, wherein the frame is operable to lock the first and second sliding members in a pre-deployment position, and wherein the frame is operable to lock the second sliding member in a post-deployment position.

16. The transcutaneous access tool insertion and retraction mechanism of claim 15, wherein the frame includes a cam element configured to lock the first and second sliding members in the pre-deployment position.

17. The transcutaneous access tool insertion and retraction mechanism of claim 16, wherein, upon deployment, the first linkage is arranged to rotate about a longitudinal axis of the torsion spring, and the first linkage and the second linkage are arranged to rotate relative to each other about a moving pivot to move the first sliding member in the insertion direction and the retraction direction.

18. The transcutaneous access tool insertion and retraction mechanism of claim 17, further comprising a release bar configured to hold the cam element when the cam element locks the first and second sliding members in the pre-deployment position and configured to release the cam element to allow the first and second sliding members to move in the insertion direction.

* * * * *